United States Patent [19]
Janzer et al.

[11] Patent Number: 5,258,166
[45] Date of Patent: Nov. 2, 1993

[54] STERILIZABLE ROLL-UP TRAY CASE

[75] Inventors: Thomas F. Janzer, 5898 Tibby Rd., Bensalem, Pa. 19020; John J. Nelson, Bristol, Pa.

[73] Assignee: Thomas F. Janzer, Bensalem, Pa.

[21] Appl. No.: 753,213

[22] Filed: Aug. 30, 1991

[51] Int. Cl.$^5$ ............................................. A61L 2/00
[52] U.S. Cl. .................................. 422/300; 422/294; 422/102; 422/104; 422/28; 206/369; 211/70.6
[58] Field of Search ............... 422/294, 300, 310, 102, 422/104, 49, 28; 206/369, 368, 370, 372, 373, 443; 433/77; 211/70.6, 69; 404/35, 36

[56] References Cited

U.S. PATENT DOCUMENTS

| | | | |
|---|---|---|---|
| 470,567 | 3/1892 | Hitch | 211/69 |
| 3,337,028 | 8/1967 | Glavan | 211/69 |
| 4,643,303 | 2/1987 | Arp et al. | 422/300 |
| 4,798,292 | 1/1989 | Hauze | 422/310 |
| 4,959,199 | 9/1990 | Brewer | 422/292 |
| 4,998,616 | 3/1991 | Hillinger | 206/372 |
| 5,004,418 | 4/1991 | Porteous | 206/369 |

Primary Examiner—Robert J. Warden
Assistant Examiner—Laura E. Collins
Attorney, Agent, or Firm—Lerner, David, Littenberg, Krumholz & Mentlik

[57] ABSTRACT

The device of the present invention is a roll up mat-like structure which may be used to retain sterile and/or contaminated tools, dental and medical instruments, probes and the like. The device is adapted to protect the tools from contamination by coming in contact with persons, inadvertently, and to minimize the risk of the transmission of infectious disease by allowing contaminated tools to come into contact with persons. The device also minimizes the risk of cross-contamination of tools. Finally, the device in accordance with the present invention is of a size and shape which will allow it to be conveniently utilized with conventional cleaning apparatus thus reducing the amount of manipulation contaminated tools require.

16 Claims, 5 Drawing Sheets

STERILIZABLE ROLL-UP TRAY CASE

FIELD OF THE INVENTION

The present invention relates to the field of containers which are useful for retaining items such that they may be conveniently displayed, sterilized and stored.

BACKGROUND OF THE INVENTION

Acquired Immune Deficiency Syndrome has raised the level of consciousness of patients with regard to the infectious disease control procedures of health care professionals. The epidemic has also heightened the awareness of health care professionals who might have otherwise felt insulated. This heightened awareness has brought with it the realization that both procedure and apparatus for dealing with potentially infected material must be improved and simplified. Every effort must be made to encourage the use of techniques and devices which will ensure the safety of both the patients and the health care provider.

Nowhere is the need for improvement greater than in the handling, storage, and processing of medical tools and probes. Dental tools are an excellent example. Dentists use a plurality of sharp ended picks and probes on almost every patient they examine. As soon as these probes are placed into the mouth of a patient, they are contaminated. Thus these tools may be the source of further transmission of, for example, the AIDS virus, hepatitis, or some form of bacterial infection.

Similarly, in handling the various dental tools, it is not uncommon for dental assistants, hygienists and dentists to stick themselves, thereby placing the tools in contact with potentially contaminated blood or placing the health care professional at risk of potential contamination from the patient.

A container which would allow for easy access to tools and which would minimize inadvertent contact with sharp and contaminated portions of the tools would, understandably, be of great use. A number of autoclavable, sterilizable dental trays and dental or medical setups are known. These include those disclosed in U.S. Pat. Nos: 846,030; 3,285,409; 857,240; 4,762,688; 4,774,063; 4,772,418; 4,798,292; and 4,865,821. These trays suffer from various shortcomings. Some, such as that disclosed in U.S. Pat. No. 4,865,821, do not include a cover element and, therefore, offer no consistent protection against inadvertently coming in contact with contaminated tools retained on the tray. Others, such as the trays described in U.S. Pat. Nos. 4,959,199 and 4,643,303, do include covers. However, these trays are generally too big to fit into such devices as particle cleaners Particle cleaners are traditionally employed to remove particles from tools before they are sterilized. As such, the tools will have to be manually placed into the particle cleaner, thus requiring undesirable and unwanted manipulation of a potentially contaminated tool. Furthermore, these trays are generally large and hold many tools. As such, it will be necessary to wait and collect a sufficient number of tools, used in treating a plurality of patients, before the tray can be used to maximum efficiency. In the interim, it is possible for a health care professional to inadvertently select an already contaminated tool or inadvertently come in contact with a contaminated tool when reaching for an uncontaminated tool on the same tray. Finally, these trays are generally too large to be used in smaller office style autoclaves. This necessitates the expenditure of capital to buy new equipment before the useful life of the old equipment has run.

Although unrelated to sterilization trays or cassettes used in the medical and dental communities, tools such as mechanics, tools are often sold in a rolled-up plastic holder which is fastened by a rope or a snap. These containers usually include a flat piece of plastic having laminated thereto a second piece of plastic. The first and the second pieces of plastic form a plurality of pockets into which each tool is slid such that it may be retained when the device is rolled up. U.S. Pat. No. 230,772 features a device of similar construction for holding pencils.

Obviously, the need for a contaminated tool holder which is small enough to retain the tools commonly necessary for the treatment of a single patient and which is of a size and shape which can readily and easily fit directly into, for example, a particle cleaner or a small autoclave, is great. Furthermore, the need for a device which can protect those persons coming in contact therewith from exposure to contaminated tools while, at the same time, protecting the tools from contamination after sterilization has been effectuated is also great. The present invention meets these needs as well as others as will be apparent from this discussion.

OBJECTS AND SUMMARY OF THE INVENTION

One object of the present invention is to provide a device which can hold medical or dental tools or probes in such a way that they may be easily displayed for use by a health care professional.

It is another object of the present invention to provide a device which can hold tools or probes and which can be readily placed into cleaning and sterilizing apparatus.

It is also an object of the present invention to provide a device which can store sterile medical probes and tools to minimize the risk of their being contaminated when not in use or when in transportation.

It is further an object of the present invention to provide a device which can minimize the risk of infection caused by inadvertent contact with contaminated tools or probes.

In accordance with these objectives, the present invention provides a device for retaining items such that they may be conveniently displayed, stored, cleaned and sterilized. The device includes a plurality of elongated members. Each of the elongated members in turn includes along the length thereof at least one pivot-coupling part and at least one pivot-receiving part. The elongated members are adapted to and may be pivotally interconnected by attaching the pivot-coupling part of one elongated member to the corresponding pivot-receiving part of the next adjacent elongated member to thereby form a mat-like structure which is capable of being rolled up and unrolled. The device also includes means associated with the elongated members for defining a plurality of gaps in the mat-like structure. The gaps are of a size and shape sufficient to allow sterilizing agents to pass therethrough. The device also includes a plurality of protruding means extending from the elongated members so as to protrude from the surface of the mat-like structure when the mat-like structure is unrolled. The protruding means are sized and disposed so as to secure in place an item placed into intimate contact with the mat-like structure and retained thereby when the device is rolled-up.

The present invention provides a roll-up type device useful for storing a number of tools such as, for, example, dental instruments, probes, scalpels and the like. The device can be unrolled such that it forms a flattened mat or tray presenting the tools contained therein to the dentist or the doctor for their use. Thereafter, and without the need to manipulate the tools further, the mat, including the tools, can be rolled up whereby the tools are retained within the roll. The rolled up mat is preferably sized and shaped such that it is adapted to fit directly into traditional office size particle cleaners such that larger debris may be removed therefrom prior to sterilization. Then, without needing to come in contact with the contaminated tools, the tools and the device can be transferred from the particle cleaner directly to an autoclave for sterilization. After sterilization, the rolled-up trays may be stored in the rolled-up position protecting the sterilized tools from inadvertent contamination. The device of the present invention may also be useful in facilitating the shipment of medical and dental tools, or even delicate non-medical items.

The present invention also encompasses a device as described in the preceding paragraphs which further includes fastening means. The fastening means will secure the mat-like device of the present invention in a rolled-up position. In a preferred embodiment, the fastening means may retain the lateral ends of the mat-like structure adjacent to one another. In this instance, and in a particularly preferred embodiment, the fastening means includes a laterally disposed terminal elongated member which is pivotally attached to one lateral end of the mat-like structure.

The device of the present invention may also include end guards disposed at first and second ends of each elongated member. The end guards are of a size and shape adapted to accommodate a defined range of pivotal movement relative to the next adjacent interconnected elongated member. Thus they help impart structural integrity and shape to the closed or rolled-up device.

In accordance with this aspect of the present invention, the mat-like device previously described can be linked to itself, one lateral end to the other lateral end, thus forming a closed shape. By the use of end guards of varying shapes, the resulting closed structure can have a cross-section in the shape of a cylinder, half a cylinder, a square, rectangle, triangle, or other convenient geometric shape. By interlocking the terminal or laterally disposed ends of the mat-like structure and providing a set shape to the device of the present invention, several advantages are realized. First, the danger of unrolling is minimized. Thus the danger of inadvertent exposure of the sterilized tools to persons or persons to contaminated tools is further minimized. Furthermore, because the device can be provided in various cross-sectional shapes, various devices can be constructed to accommodate a wide variety of cleaning and sterilizing apparatus as well as a wide variety of tools probes and/or medical or dental instruments. These shapes will also allow for the device of the present invention to be more easily stacked, stored, and transported or shipped.

In one preferred aspect of the present invention, the device forms a cylinder when in a rolled-up position. In another preferred embodiment, the device forms a half cylinder or semi-circle in cross-section when in a rolled-up position.

BRIEF DESCRIPTION OF THE DRAWINGS

The foregoing will be better understood with reference to the following examples. These examples are for the purposes of illustration. They are not to be considered limiting as to the scope and nature of the present invention.

DETAILED DESCRIPTION OF THE PREFERRED EMBODIMENT

In its most basic form, the device of the present invention is composed of a plurality of individual elongated members which are pivotally interconnected to their next adjacent neighbors such that they form a mat-like structure that is flexible and can be rolled up and unrolled. In one aspect as used herein, the terms "rolled" and "rolled up" include the general configuration obtained by rolling a newspaper or magazine such that one lateral end of the mat-like structure of the device is disposed at the center of the roll and a second lateral end is on the periphery of the rolled up item. Another use of the terms in accordance with the present invention encompasses the joining of the two laterally disposed ends of the device such that a polygon or closed curved structure is formed by the cross-section of the resulting structure. "Rolled up", particularly in the latter context, does not mean that the item will have a cross-section which is generally round. However, such a structure is generally preferable.

Figure 2:
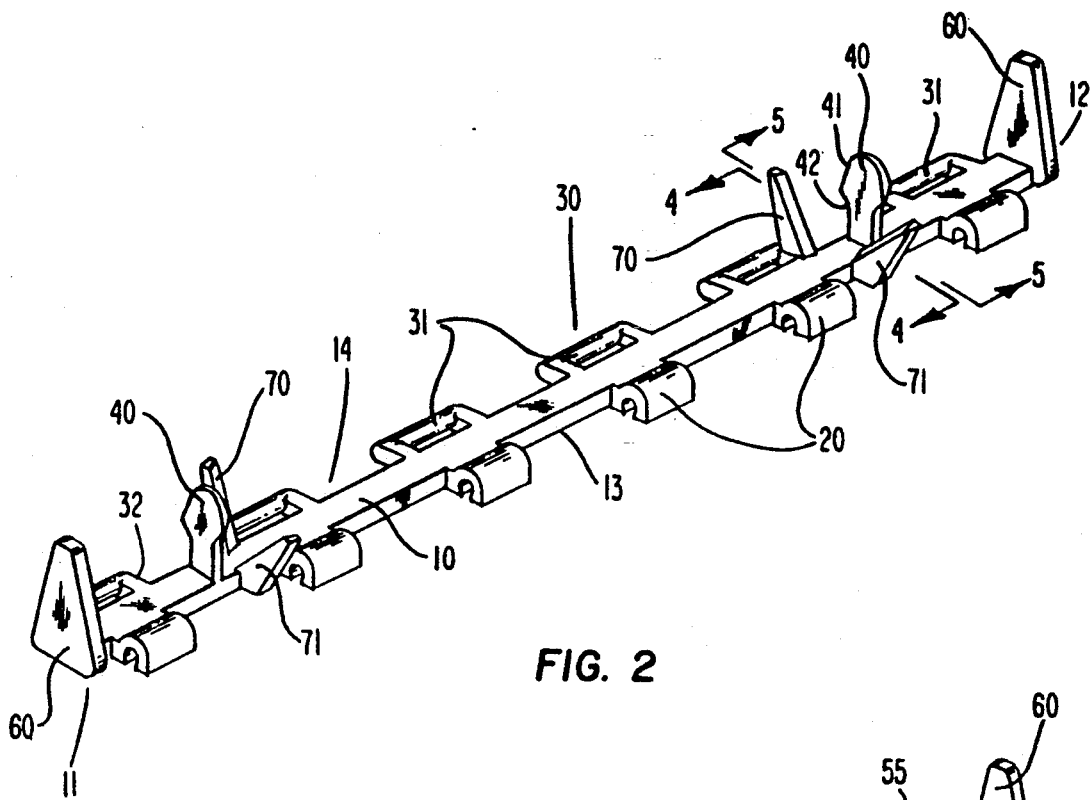
FIG. 2 is a perspective view of an elongated member used to construct the device illustrated in FIG. 1.
Figure 5:
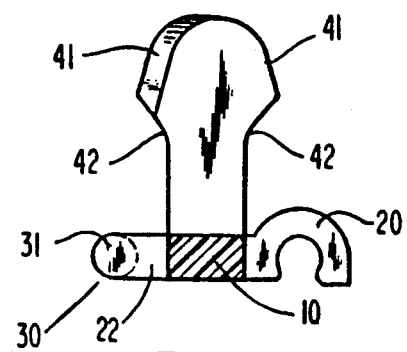
FIG. 5 is a cross-sectional view of elongated member 10 taken along Line 5—5 of FIG. 2.
Figure 9:
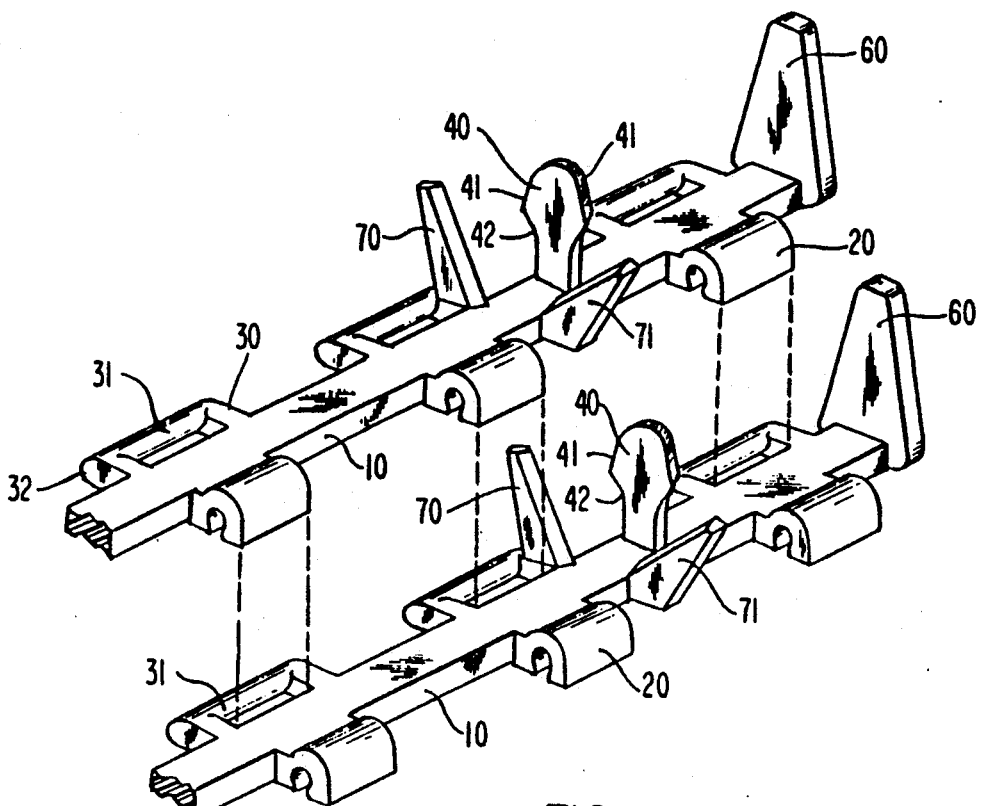
FIG. 9 is an exploded perspective view of two elongated members illustrating their interconnection.
Figure 10:
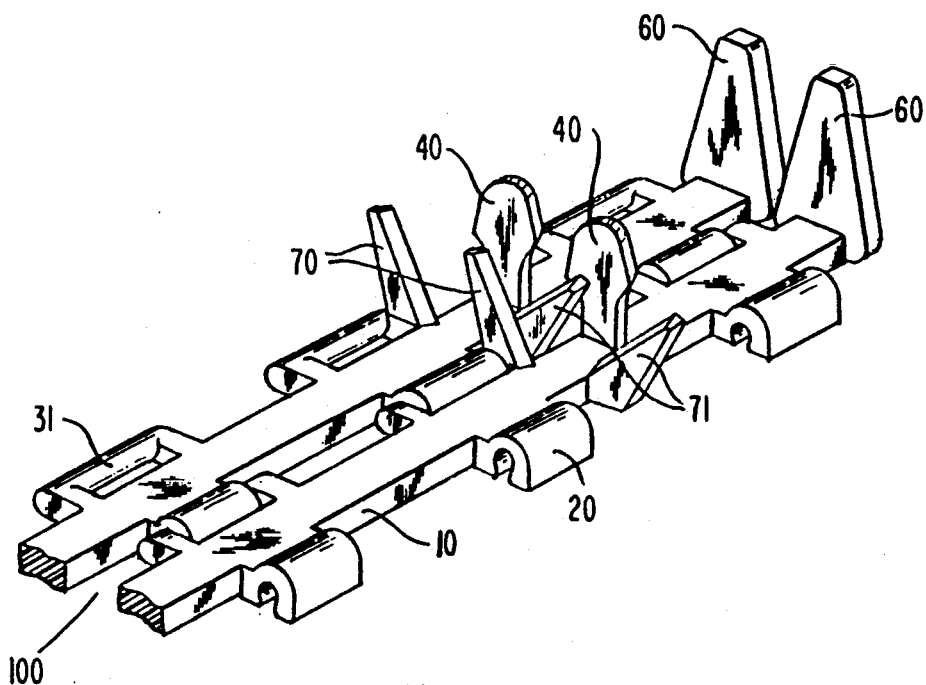
FIG. 10 is a perspective view of two elongated members when interconnected.
Figure 11:
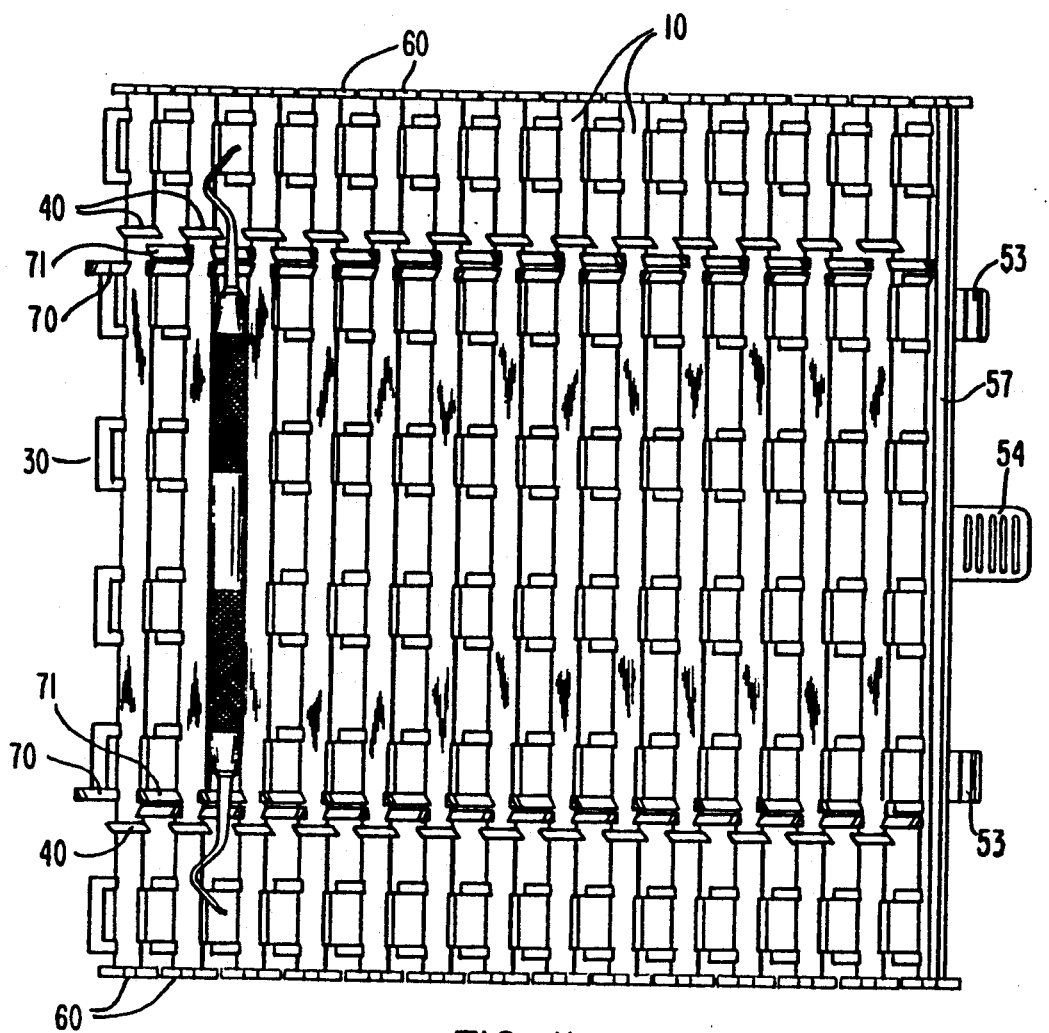
FIG. 11 is a top plan view of the mat-like structure of a preferred embodiment of the device of the present invention.
Figure 12:
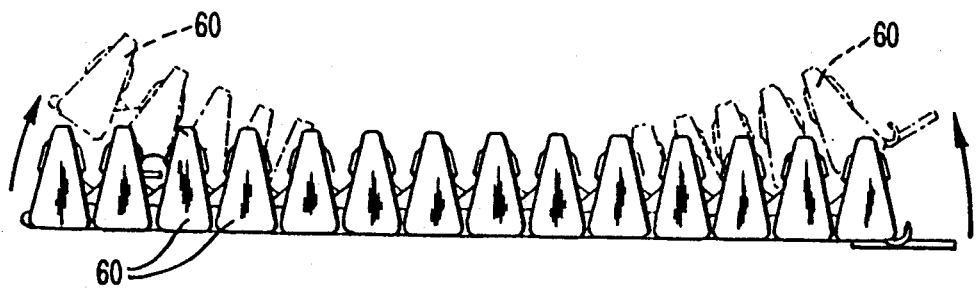
FIG. 12 is an end view of the structure illustrated in FIG. 11, and showing, in dashed outline, the manner in which the mat-like structure is rolled up.
Figure 13:
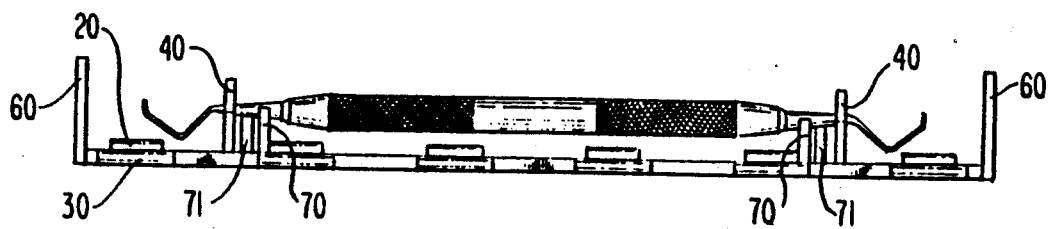
FIG. 13 is a lateral side view of the mat-like structure shown in FIG. 11.

As illustrated in FIG. 11, the mat-like structure may be made up of a plurality of elongated members 10. Each of the elongated members 10 has a first longitudinal end 11, a second end 12, and a pair of lateral sides 13 and 14 respectively (FIG. 2). Each of the elongated members 10 are adjoined to the next adjacent elongated member 10 so as to form the mat-like structure (FIG. 9 and FIG. 10). In addition, elongated members 10 are interconnected in such a way that some freedom of movement is retained with regard to one another. Preferably, members 10 are interconnected by a pivot means. The pivot means may facilitate the permanent, but pivotally movable, joining of the elongated members 10 or may allow for each elongated member 10 to be pivotally, but releasably, fastenable to one another. To accomplish the latter, each elongated member 10 may be provided with at least one pivot-coupling part 20 (FIG. 5 and FIG. 2) and at least one pivot-receiving part 30 (FIG. 5 and FIG. 2). The pivot-receiving part 30 preferably comprises a cylindrical post 31 which is disposed roughly parallel to elongated member 10. Post 31 is spaced laterally from elongated member 10 by a pair of legs 32 which join post 3 with lateral side 14 of elongated member 10 (FIG. 2). It is preferable that each elongated member 10 contain at least two and preferably three pivot-receiving parts 30. Most preferably, however, the device of the present invention includes elongated members 10 having at least six pivot-receiving parts 30 spaced equally along the length thereof.

Disposed laterally across from pivot-receiving parts 30 and in a position which facilitates cooperation with pivot-receiving parts 30 on the next adjacent elongated member 10, are pivot-coupling parts 20 which are attached to lateral side 13 of elongated member 10. Pivotal-coupling part 20 includes a generally U-shaped piece having a recess 21 which is adapted to engage and couple to post 31 of the pivot-receiving part 30 of the next adjacent elongated member 10. In the preferred embodiment described herein, the pivot-coupling members 20 merely "snaps onto" the post 31 of the corresponding pivot-receiving parts 30 thus forming a pivotal interconnection.

Figure 1:
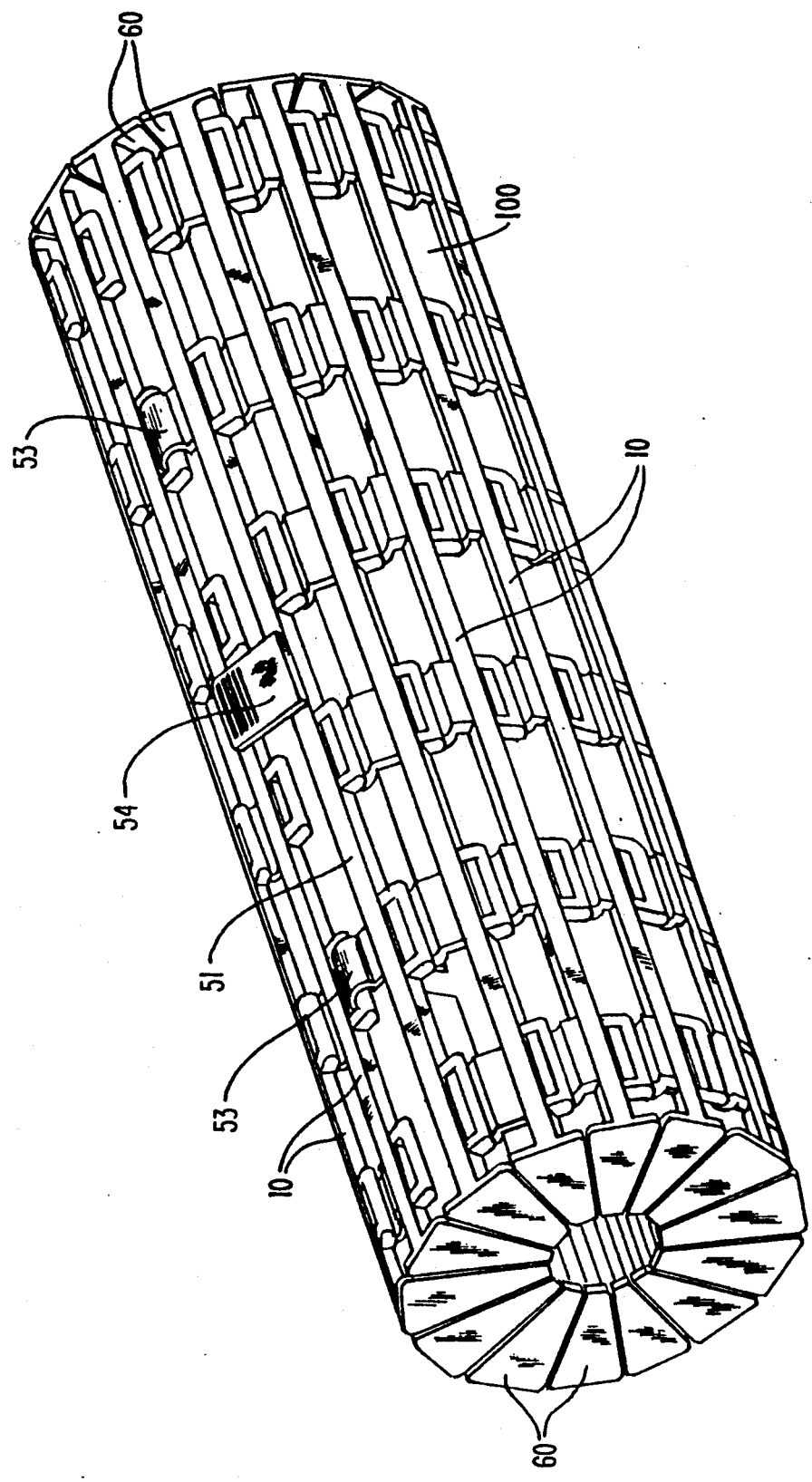
FIG. 1 is a perspective view of a preferred embodiment of the device of the present invention showed in a rolled-up configuration.

Because both the pivot-coupling part 20 and the pivot-receiving part 30 are laterally spaced with regard to their respective elongated members 10, each adjacent elongated member is spaced apart from each other. The joined laterally disposed pivot-coupling part 20 and pivot-receiving part 30 thereby define a plurality of gaps 100. Thus, it is possible to consider the joined pivot-coupling parts 20 and the pivot-receiving parts 30 as means defining gaps 100 (FIG. 1 and FIG. 10). It is preferable that the gaps 100 be of sufficient size and shape to allow sterilizing agents or cleaning agents to pass through the mat-like structure when rolled up. In this way, particulate and debris may be cleaned and carried away and drained from the device of the present invention when in a rolled-up configuration. Furthermore, this ensures that free contact with sterilizing material such that sterilization will be complete and efficient. Other means for defining a plurality of gaps can also be envisioned such as a plurality of apertures contained within elongated members 10.

The elongated members 10 of the present invention are also provided with a plurality of protruding means 40 which assist the mat-like device of the present invention in retaining items placed into intimate contact therewith (FIG. 5 and FIG. 2). This is particularly true when the mat-like structure of the device of the present invention is in the process of being rolled up. Furthermore, these protruding means 40 prevent unwanted shifting of the position of the items secured within the mat-like structure. The protruding means 40 may be as simple in design, as a trapezoidal shaped member or other similarly structured piece which will not prevent or impede the rolling or closing of the mat-like structure of the device of the present invention but which will abut and assist in retaining tools. However, in a particularly preferred embodiment and as illustrated in FIG. 5, the protruding means 40 have a shape which is similar to the cross-section of a mushroom. The protruding means 40 include a plurality of cooperating tapering edges 41 on the widest portion thereof or the ends of the cap of the mushroom. These cooperating tapering edges 41 allow one protruding means to snugly abut the next adjacent protruding means 40 of the next adjacent elongated member 10 of a mat-like structure when the device is rolled up. Each protruding means 40 also includes a plurality of retaining recesses or lips 42. The retaining recesses 42 are defined by the gradual widening of the body of the protruding means 40 between the elongated member 10 and the cap of the mushroom-shaped portion of protruding means 40. Protruding means 40 can, in alternative embodiments, have other shapes such as, for example, a "T". The top, or cross of the T, would include the plurality of cooperating tapering edges 41 at the ends of the cross portion such that when the mat-like structure is rolled up, the ends of the T structure would abut one another. The junction of the cross of the T and the body of the protruding member 40, generally forming a right angle, would represent and define the retaining recess 42.

Figure 7:
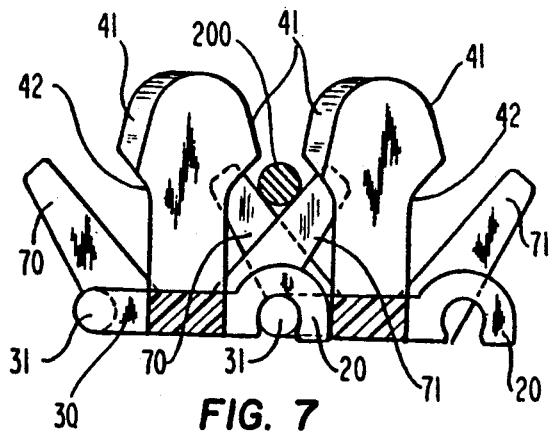
FIG. 7 is a cross-sectional view of two interconnected elongated members, illustrating such members in the unrolled configuration.
Figure 8:
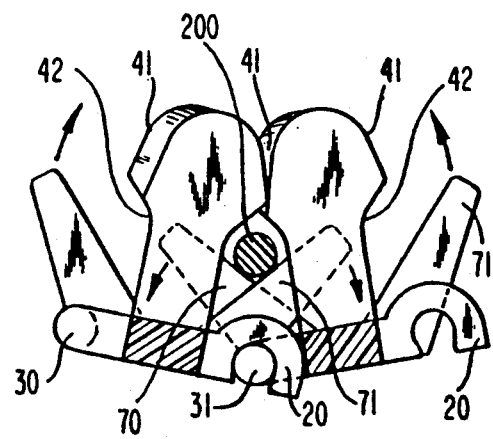
FIG. 8 is a cross-sectional view of two interconnected elongated members similar to FIG. 7 but illustrating such members in the rolled-up configuration.

The protruding means 40 thus have a relatively wider and a relatively narrower portion. In use, an item is placed between two adjacent protruding members 40 and when the mat-like structure is rolled up, the wider portions of the protruding members 40 are brought into intimate contact with one another and cooperatively abut at the cooperating tapering edges 41. A gap 200 is formed between the two adjacent narrower portions of the protruding members 40 (FIG. 7 and FIG. 8). It is within this gap 200 that the item placed into intimate contact with the mat-like structure is locked into place.

The device of the present invention may also be advantageously provided with a fastening means 50. The fastening means may be something as simple as a piece of string which, when tied around the rolled-up device, will retain it in a rolled-up configuration. Similarly, a rubber band, tape or a wrap around band made of velcro could be used as the retaining means 50. Alternatively, the device of the present invention could be releasably fastened, such that it is fastenable and unfastenable, by affixing a velcro patch to one side of one end of the mat-like structure and affixing a corresponding velcro patch on the other side of the mat-like structure. When rolled up, the device of the present invention would position the corresponding velcro patches adjacent to each other such that they could be attached and retain the device in a rolled-up configuration.

In one embodiment of the present invention, the mat-like structure may be rolled up such that its lateral ends meet. This is to say that the lateral side 13 of elongated member 10 forming one lateral end of the mat-like structure is connected, directly or indirectly, to lateral side 14 of the elongated member 10 forming the other lateral end of the structure. In other words, the first and the last elongated members 10 are directly or indirectly interconnected. This may be accomplished by equipping the corresponding lateral ends of the mat-like structure with cooperating male and female members, a hook and latch, a plurality of posts which may be tied together and the like. Furthermore, one lateral end of the mat could be provided on one side with velcro and the other lateral end could have attached thereto a flap of velcro which extends laterally beyond the end of the mat. Thus, when the lateral ends of the mat are brought into sufficiently close proximity to each other, the velcro flap on one lateral end of the mat could be brought into cooperative and intimate contact with the velcro patch on the other lateral end of the mat-like structure and the two ends would thus be joined thereby.

Figure 3:
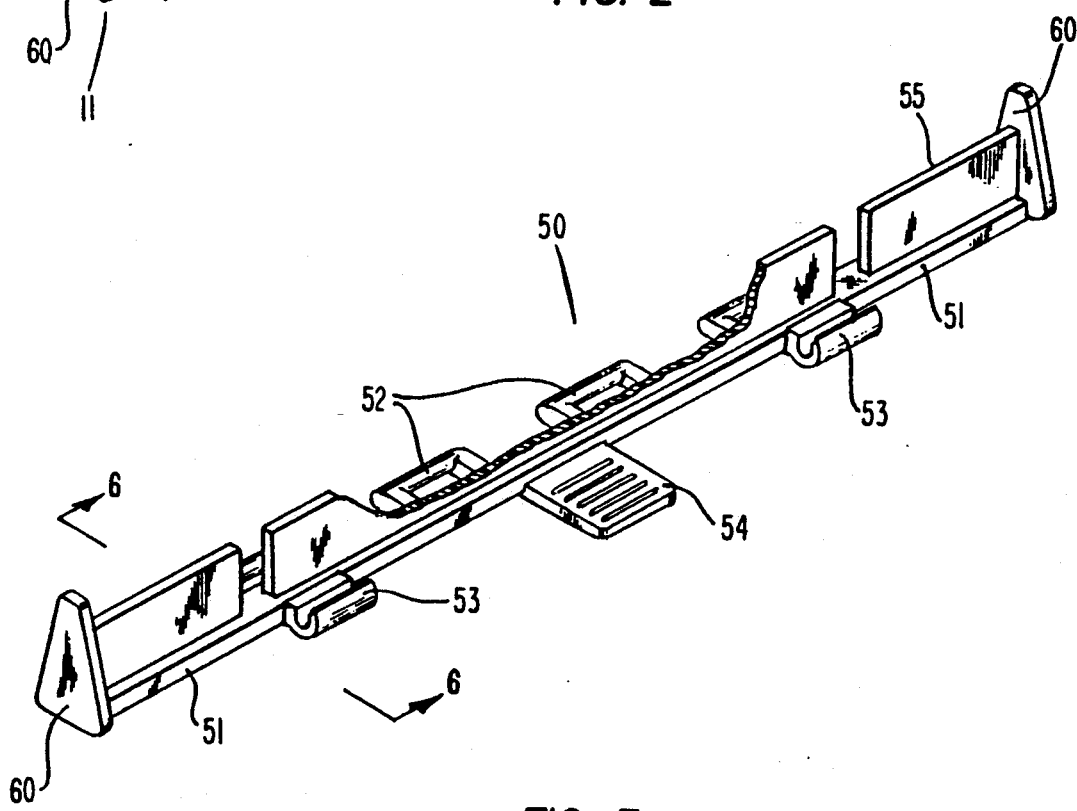
FIG. 3 is a perspective view of a preferred fastening means employed in the device illustrated in FIG. 1.

In a preferred embodiment, however, fastening means 50 includes a terminal elongated member 51 which is similar in size and shape to the elongated members 10 (FIG. 3). The terminal elongated member 51 should include at least one pivot-receiving part 52 which is positioned to receive at least one pivot-coupling part 20 located on the elongated member 10 forming the lateral end of the mat-like structure. Thus the terminal elongated member 51 may be pivotally attached to the next adjacent elongated member 10 and thereby to the mat-like structure in the same manner as each elongated member 10 is pivotally connected to its next adjacent neighbors. The fastening means 50 including terminal elongated member 51 may also include at least one pivot-coupling part 53 which is adapted to engage a pivot-receiving part 30 of the elongated member 10 defining the other or opposite lateral end of the mat-like structure i.e. the pivot-receiving part 30 of the first elongated member 10 (FIG. 1).

In a particularly preferred embodiment, the terminal elongated member 51 will have the sam number of pivot-receiving parts 52 as the number of pivot-coupling parts 20 found on each of the elongated members 10. Thus if each elongated member 10 has six equally spaced coupling parts 20, the terminal elongated member 51 will have six corresponding and equally spaced pivot-receiving parts 52.

This is not true, however, for the pivot-coupling part 53 included on terminal elongated member 50. It is preferable that the number of pivotal-coupling parts 53 included thereon be less than the number of pivot-receiving parts 30 found on elongated members 10. In fact, when the number of pivot-receiving parts 30 contained on elongated member 10 is six, the number of pivot-coupling parts 53 included on terminal elongated number 50 should be limited to two or three. This number will provide sufficient stability to the structure when in a rolled-up and fastened configuration but will not provide so much resistance as to render the device difficult to open and unroll. It is also preferable that the junction between the two lateral ends of the mat-like structure of the device of the present invention be easier to connect and disconnect than connecting and disconnecting individual elongated members 10. The provision of fewer pivot-coupling parts 53 on terminal elongated member 51 will accomplish this objective.

It is of no importance that the elongated member 10 forming the other or opposite lateral end of the mat-like structure will thus have pivot-receiving parts 30 which have no corresponding pivot-coupling part 53 on the terminal elongated member 51.

Terminal elongated member 51 may also have a tab 54 which will assist an operator in manipulating the fastening means 50. This tab 54 may also act as a brace to prevent the rolled-up device from moving when placed onto a flat surface. Of course, other structures may be added to the exterior of the device to limit its ability to move when in the rolled-up position, for example, a flatsided ridge could be added to the outer side of the mat-like structure to prevent rolling. Terminal elongated member 51 may also include a supporting ridge 55 to give additional support at the point at which the lateral ends of the device of the present invention are joined.

Figure 6:
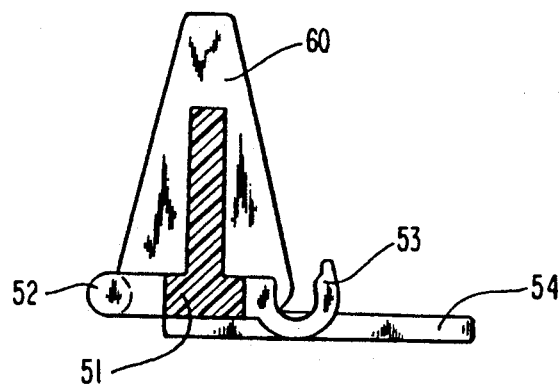
FIG. 6 is a cross-sectional view of the fastening means illustrated in FIG. 1 taken along Line 6—6 of FIG. 3.

End guards 60 may also be useful in accordance with the present invention and they are preferably located at the ends 11 and 12 of each elongated member 10 and at the corresponding ends of terminal elongated member 51, when such a member is present (FIG. 2, FIG. 3, FIG. 6). The end guards 60 are of a size and shape adapted to impart a defined range of pivotal movement to the next adjacent interconnected elongated member 10. Thus when two elongated members 10 are joined as illustrated in FIG. 10 and FIG. 1, the end guards 60 of each adjacent interconnected elongated member 10 abut each other when the mat-like structure is rolled up. By one end guard 60 coming into physical contact with the next adjacent end guard 60, further pivotal movement in that direction by the elongated members 10 is restricted.

End guards 60 also aid in imparting a specific shape to the rolled-up mat-like structure. As shown in FIG. I, when the end guards 60 are generally trapezoidal, the cooperation of the various end guards 60 forms a flat disc shaped plate. When so constructed, each individual end guard 60 abuts another end guard 60 on each side of it. Thus each end guard 60 supports its adjacent end guards 60, and vice versa. The resulting complete structure (i.e. the disc), provides structural integrity and shape to the device of the present invention (in this case, a cylinder). Of course, the device of the present invention need not form a cylinder. In fact, the end guards 60 can be so configured such that the cross-section of the resulting structure has the shape of any regular polygon, i.e. triangle, square, rectangle, trapezoid, parallelogram, octagon and the like or any closed curved structure (eg. oval, egg-shaped). This would require that certain end guards 60 be of differing sizes and shapes to accommodate, for example, flat sides and corners.

End guards 60 also provide an additional measure of protection. The end guards 60 aid in retaining items within the lumen formed when the mat-like structure is rolled up. This prevents instruments from being inadvertently released from the device of the present invention and protects the tools contained therein from inadvertent contamination and/or protects people from coming in contact with contaminated tools.

Figure 4:
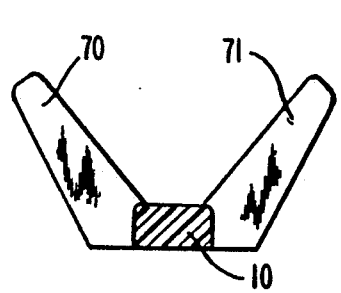
FIG. 4 is a cross-sectional view of elongated member 10 taken along Line 4—4 of FIG. 2.

Finally, in accordance with a preferred embodiment of the present invention, each individual elongated member 10 may include a plurality of seating members 71 and 70 (FIG. 4). These seating members are angled fingers extending laterally and generally upwardly away from the inner surface of the mat-like structure. As illustrated in FIG. 7-FIG. 10, when two elongated members 10 are interconnected as described herein, the seating member 71 of one elongated member 10 will cross the path of the seating member 70 of the next adjacent elongated member 10 in much the same way as two swords that are crossed. It is not necessary, however, that the seating members touch one another.

When viewed from the side, the crossed seating member 71 from a first elongated member 10 and seating member 70 from the next adjacent elongated member appeared to form an "X". The top of the "X" is V-shaped and it is within this resulting "V" that the tools or other items to be retained within the device of the present invention are seated. Because of the orientation of seating members 71 and 70, the tool is constantly urged towards the base or vertex of the V-shaped seat such that it is retained in the center thereof.

As illustrated in FIG. 7 and FIG. 8, when two adjacent elongated members 10 are rotated with respect to one another, the V-shaped seat begins to flatten out. That is to say that the angle at the vertex of the "V" becomes more obtuse. At the same time, the point of intersection of seating members 71 and 70 (i.e. the point at which they "cross" each other's path) is altered such that the tool contained within the seat lowers or recedes toward the inner surface of the mat-like structure. When the mat-like structure is unrolled, the opposite phenomena occurs. Specifically, the angle of the vertex of the "V" becomes more acute and the tool is once again elevated with respect to the inner surface of the mat-like structure. As such, the device of the present invention draws a tool in to retain it and raises the tool up for presentation when the device is opened for use.

In operation a tool is placed into the V-shaped seat formed by seating members 71 and 70 on adjacent interconnected members 10. This V-shaped seat is located in gap 200 located between adjacent protruding means 40. When the mat-like structure is closing, each interconnected member 10 rotates with regard to its next adjacent neighbor. Simultaneously, the end guards 60 of adjacent elongated members 10 are brought into intimate contact as are the cooperating tapering edges 41 on adjacent protruding means 40. Also, the seating members 71 and 70 on adjacent elongated members 10 rotate away from each other such that the angle of the vertex of the seat increases. The end guards 60 eventually stop the relative movement of one elongated member with regard to the other. At that point, protruding members 40 are in intimate contact with one another via their respective cooperating tapering edges and a gap 200 is totally enclosed thereby. The tool or item retained is seated on a seat created by seating members 71 and 70 of adjacent elongated members 10 and rests within the gap 200 between the adjacent and cooperating protruding means 40. The seating members and the seat serve urge the tool into intimate contact with the retaining recesses 42 of the protruding means 40 such that the degree of movement of the tool is severely restricted. They also prevent the tool or item from slipping through gaps 100 formed between adjacent elongated members 10. When the device of the present invention is unrolled, and laid flat upon a surface such as a table top, the retained tools are prominently displayed and accessible to the user.

In a preferred embodiment in accordance with the preferred invention, the cross-section of the device is that of a half-circle. In such instance, fastening means 50 includes a terminal elongated member 51 which is an extended flat plate which can traverse the gap between the two lateral ends of the mat-like structure. In such configuration, the device has fewer elongated members 10 interconnected to form a mat-like structure. In fact, a device in accordance with this aspect of the present invention includes only enough elongated members 10 to allow the formation of a mat having a hemispheric, or half-circular cross-section. The extended plate of the terminal elongated member 51 will further include pivot-coupling parts 53 which are adapted to be reversibly fastenable and unfastenable to the pivot-receiving parts 30 of the opposite lateral end of the mat-like structure. In a particularly preferred embodiment, the plate includes a plurality of apertures through which cleaning or sterilizing solution may freely flow into and out of the device. This embodiment may be particularly useful when few tools are required and/or when the use of a flat bottom is preferable to accommodate the confines of a particular autoclave or for stacking the device of the present invention on the shelf.

The principles, preferred embodiments, and modes of operation of the present invention have been described in the foregoing specification. The invention which is intended to be protected herein, however, is not to be construed as limited to the particular embodiments disclosed, since these are to be regarded illustrative rather than restrictive. Variations and changes may be made by others without departing from the spirit and scope of the invention.

What is claimed is:

1. A device for retaining items such that they may be conveniently displayed, stored, cleaned and sterilized comprising: A plurality of elongated members, each of said elongated members including along the length thereof at least one pivot-coupling part and at least one pivot-receiving part, said elongated members being adapted to pivotally interconnect by attaching said pivot-coupling part of said elongated member to the corresponding pivot-receiving part of a next adjacent elongated member, said elongated members being such that a plurality of interconnected elongated members form a mat structure which is capable of being rolled up and unrolled; means associated with said elongated members for defining a plurality of gaps in said mat structure which are of a size and shape sufficient to allow sterilizing agents to pass therethrough; and a plurality of protruding means extending from said elongated members so as to protrude from the surface of said mat structure when said mat structure is unrolled, said protruding means being sized and disposed so as to secure and place an item placed into intimate contact with said mat structure and retained thereby when said mat structure is rolled-up.

2. The device of claim 1 further comprising fastening means for maintaining said mat structure in a rolled-up and fastened configuration.

3. The device of claim 2 wherein said fastening means further comprises a terminal elongated member, said terminal elongated member being interconnected to a first lateral end of said mat structure.

4. The device of claim 3 wherein said terminal elongated member is adapted to be releasably fastenable to a second lateral end of said mat structure such that when in the rolled-up and fastened configuration, lateral ends of said mat structure are interconnected.

5. The device of claim 1 wherein said protruding means include a plurality of cooperative tapering edges and a plurality of item retaining recesses.

6. The device of claim 1 further comprising at least one end guard disposed at at least one end of said elongated members.

7. The device of claim 5 wherein said protruding means includes a plurality of retaining recesses or lips.

8. The device of claim 6 wherein said at least one guard defines an arced portion of the circumference of a cylinder and wherein said mat structure includes sufficient elongated members to form said cylinder when rolled up and when a first lateral end and a second lateral end of said mat are interconnected by a fastening means.

9. The device of claim 8 wherein said at least one end guard defines an arced portion of the circumference of said cylinder and wherein said mat structure includes sufficient elongated members to form a half-cylinder when rolled up and when said first and said second lateral ends are interconnected by said fastening means.

10. The device of claim 9 further comprising a terminal elongated member including a plate, said plate having a size and shape sufficient to cooperate with said mat structure to form a semi-circle when said mat structure is rolled up.

11. The device of claim 10 wherein said plate includes a plurality of slots to allow sterilizing agents to pass therethrough.

12. The device of claim 1 wherein each of the plurality of elongated members includes along its length a plurality of pivot-coupling parts and corresponding pivot-receiving parts.

13. The device of claim 12 wherein each of said plurality of elongated members includes along the length thereof at least three pivot-coupling parts and at least three pivot-receiving parts.

14. The device of claim 13 wherein each of said plurality of elongated members includes along the length thereof at least six pivot-coupling parts and at least six pivot-receiving parts.

15. The device of claim 1 further comprising a plurality of seating members emanating from adjacent elongated members for receiving and supporting said item placed on said mat structure, said seating members supporting said item in a first raised position when said mat structure is unrolled and supporting said item in a second lowered position when said mat structure is rolled up.

16. A device for retaining items such that they may be conveniently displayed, stored, cleaned and sterilized comprising a plurality of elongated members, each of said elongated members including along the length thereof at least three equally spaced pivot-coupling parts and at least three equally spaced pivot-receiving parts, said elongated members being adapted to pivotally interconnect by attaching said pivot-coupling parts of said elongated members to the corresponding pivot-receiving parts of a next adjacent elongated member, said elongated members being such that a plurality of interconnected elongated members form a mat structure which is capable of being rolled up and unrolled; means associated with said elongated members for defining a plurality of gaps in said mat structure which are of a size and shape sufficient to allow sterilizing agents to pass therethrough; a plurality of protruding means including a plurality of cooperative tapering edges and a plurality of item-retaining recesses extending from said elongated members so as to protrude from the surface of said mat structure when said mat structure is unrolled, said protruding means being sized and disposed so as to secure in place an item placed into said plurality of item-retaining recesses defined thereby; a plurality of seating members emanating from said elongated members positioned so as to receive and support said item disposed thereon in said plurality of item retaining recesses defined by said protruding means; and fastening means including a terminal elongated member which is interconnected to one lateral end of said mat structure and which is adapted to be releasably fastenable to a second lateral end of said mat structure such that when in a rolled up and fastened configuration, lateral ends of said mat structure are interconnected.

* * * * *

UNITED STATES PATENT AND TRADEMARK OFFICE
CERTIFICATE OF CORRECTION

PATENT NO. : 5,258,166
DATED : November 2, 1993
INVENTOR(S) : Janzer et al.

It is certified that error appears in the above-indentified patent and that said Letters Patent is hereby corrected as shown below:

Column 1, line 53, after the first occurrence of the word "cleaners", insert --.--.
Column 2, line 5, "mechanics" should read --mechanics'--.
Column 5, line 16, "post 3" should read --post 31--.
Column 7, line 28, "sam" should read --same--.

Signed and Sealed this

Seventh Day of February, 1995

Attest:

BRUCE LEHMAN

Attesting Officer

Commissioner of Patents and Trademarks